United States Patent
Jeong et al.

(10) Patent No.: US 7,692,021 B2
(45) Date of Patent: Apr. 6, 2010

(54) NPN-TYPE LOW MOLECULAR AROMATIC RING COMPOUNDS AND ORGANIC SEMICONDUCTORS AND ELECTRONIC DEVICES INCORPORATING SUCH COMPOUNDS

(75) Inventors: Eun Jeong Jeong, Seongnam-Si (KR); Joo Young Kim, Suwon-Si (KR); Hyun Sik Moon, Seoul (KR); Bang Lin Lee, Suwon-Si (KR); Kook Min Han, Suwon-Si (KR); Eun Kyung Lee, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 95 days.

(21) Appl. No.: 11/508,925

(22) Filed: Aug. 24, 2006

(65) Prior Publication Data

US 2007/0166871 A1 Jul. 19, 2007

(30) Foreign Application Priority Data

Jan. 17, 2006 (KR) .................... 10-2006-0004916

(51) Int. Cl.
*C07D 277/20* (2006.01)
*C07D 277/60* (2006.01)
(52) U.S. Cl. ...................... 548/156; 548/202
(58) Field of Classification Search ............. 548/202
See application file for complete search history.

(56) References Cited

OTHER PUBLICATIONS

RN 212267-26-0, retrieved from CAPLUS on May 5, 2008.*
RN 372190-92-6, retrieved from CAPLUS search on Nov. 19, 2008.*

A. Afzali et al. "High-Performance, Solution-Processed Organic Thin Film Transistors From A Novel Pentacene Precursor" JACS Communications (2002).
A. R. Murphy et al. "Organic Thin Film Transistors From A Soluble Oligothiophene Derivative Containing Thermally Removable Solubilizing Groups" JACS Communications (2003).
W. Li et al. "Field-Effect Transistors Based On Thiophene Hexamer Analogues With Diminished Electron Donor Strength" Chem. Mater. (1999).
X. M. Hong et al. "Thiophene-Phenylene and Thiophene-Thiazole Oligomeric Semiconductors With High Field-Effect Transistor On/Off Ratios" Chem. Mater. (2001).

* cited by examiner

*Primary Examiner*—Rebecca L Anderson
*Assistant Examiner*—Shawquia Young
(74) *Attorney, Agent, or Firm*—Harness, Dickey & Pierce, P.L.C.

(57) ABSTRACT

Disclosed herein are NPN-type low molecular aromatic ring compounds, organic semiconductor layers formed from such compounds that exhibit improved electrical stability and methods of forming such layers using solution-based processes, for example, spin coating processes performed at or near room temperature. These NPN-type compounds may be used, either singly or in combination, for fabricating organic semiconductor layers in electronic devices. The NPN-type aromatic ring compounds according to example embodiments may be deposited as a solution on a range of substrates to form a coating film that is then subjected to a thermal treatment to form a semiconductor thin film across large substrate surfaces that exhibits reduced leakage currents relative to conventional PNP-type organic semiconductor materials, thus improving the electrical properties of the resulting devices.

7 Claims, 2 Drawing Sheets

Complete conjugation system

NPN-TYPE LOW MOLECULAR AROMATIC RING COMPOUNDS AND ORGANIC SEMICONDUCTORS AND ELECTRONIC DEVICES INCORPORATING SUCH COMPOUNDS

PRIORITY STATEMENT

This non-provisional application claims priority under 35 U.S.C. § 119(a) from Korean Patent Application No. 2006-4916, which was filed on Jan. 17, 2006, and which is herein incorporated, in its entirety, by reference.

BACKGROUND

1. Field

Example embodiments relate, generally, to an NPN-type organic compounds, and organic semiconductor films and electronic devices fabricated using such compounds, for example, to NPN-type low molecular aromatic ring compounds, organic semiconductor films formed from such compounds via a solution-based process for example, spin coating at room temperature, and electronic devices including such organic semiconductor films.

2. Description of the Related Art

Flat display devices, for example, liquid crystal display devices and organic electroluminescent display devices, are typically provided with one or more types of thin film transistors for controlling the operation of the display devices. The basic thin film transistor structure comprises a gate electrode, source/drain electrodes, and a semiconductor layer forming a channel region in which the conductivity can be controlled through the operation of the gate electrode. The p-type or n-type semiconductor layer functions as conductive channel material through which current will flow between the source and drain electrodes when an appropriate voltage level is applied to the gate electrode.

Various low molecular weight organic materials, for example, pentacene, have been investigated for use as organic semiconductor materials. As a result of these investigations, the properties and electrical behavior of various such organic materials have been determined. Pentacene, for example, has been reported to have a charge mobility in the range of 3.2 to 5.0 $cm^2/V \cdot s$ or perhaps more, but has also been deemed unsuitable for general fabrication processes as a result of the costs and complexity associated with the formation of such a film over larger areas, the need for expensive vacuum deposition equipment for forming the thin film and the difficulties in forming a fine pattern from the thin film.

On the other hand, certain other polymeric or oligomeric organic semiconductors, while tending to exhibit lower charge mobility levels than other low molecular weight organic materials, for example, pentacene, can provide cost advantages as a result of the relatively simple processing, for example, spin coating, that can be used to form thin films of these materials over relatively large substrate areas. As such an organic semiconductor, a soluble pentacene precursor capable of being annealed at about 120-200° C. and exhibiting a charge mobility of about 0.1 $cm^2/V \cdot s$ has been reported. In addition, an oligothiophene precursor, which has charge mobility of 0.03-0.05 $cm^2/V \cdot s$ and may be annealed at 180-200° C., was reported.

Further, PNP-type oligothiophenes having an N-type core have been reported as exhibiting a charge mobility of about 0.00001-0.01 $cm^2/V \cdot s$ when using bithiazole as a core, or when configured as a thiophene ring and a benzene ring using thiazole as a core.

However, the PNP-type oligothiophenes mentioned above still tend to be considered less suitable for general fabrication processes because they require the use of vacuum deposition processes for forming a thin film and, further, their P-type $\pi$-conjugation is discontinuous as a result of the N-type core. Thus, even though the number of thiophene rings is increased, in the on-state the current flows tend to be unduly limited, and in the off-state the leakage levels tend to be difficult to maintain at a sufficiently low level. The observed leakage levels have generally been attributed, at least in part, to the increased oxidation potential associated with the increased number of thiophene rings.

SUMMARY

The compounds according to example embodiments have been developed to provide improved NPN-type compounds suitable for integration into general semiconductor fabrication processes and which also address certain of the deficiencies associated with the conventional organic semiconductor materials noted above. The NPN-type compounds according to example embodiments are suitable for application to substrates via solution-based processes, for example, spin coating, for forming coating layers at temperatures at or near room temperature, and are capable of being converted to organic semiconductor layers via relatively low temperature thermal treatments utilizing, for example, treatment temperatures of less than 200° C. or even less than 150° C.

The availability of this lower temperature and solution-based processing can be utilized to reduce the capital and operational expenses relative to certain other organic semiconductor materials and render the NPN-type compounds according to example embodiments suitable for use with a wider range of substrate materials. The NPN-type compounds according to example embodiments are also structured to provide organic semiconductor thin films exhibiting improved chemical and electrical stability that can, in turn, result in improved device performance and reliability for those devices that incorporate such films as a carrier transport layer.

The compounds according to the invention are NPN-type aromatic ring compounds which may be generally represented by Formula I:

$$(A_1)\text{-}(X)_n\text{-}(A_2) \qquad (I)$$

wherein each X is independently selected from a group consisting of unsubstituted and substituted C6-C30 aryl groups, unsubstituted and substituted C2-C20 heteroaryl groups containing sulfur (S) or selenium (Se), $A_1$ and $A_2$ are each independently selected from a group consisting of C2-C20 heteroaryl groups that contain nitrogen (N) or oxygen (O), and wherein n is an integer from 2 to 10.

In addition, the invention provides for organic semiconductors formed using the above-mentioned aromatic ring compounds, and electronic devices including such organic semiconductors as a carrier transport layer.

BRIEF DESCRIPTION OF THE DRAWINGS

Example embodiments of the NPN-type aromatic ring compounds and example embodiments of organic semiconductor layers formed from these compounds, active structures incorporating such organic semiconductor layers and semiconductor devices incorporating such structures are addressed more fully below with reference to the attached drawings in which.

Figure 1:
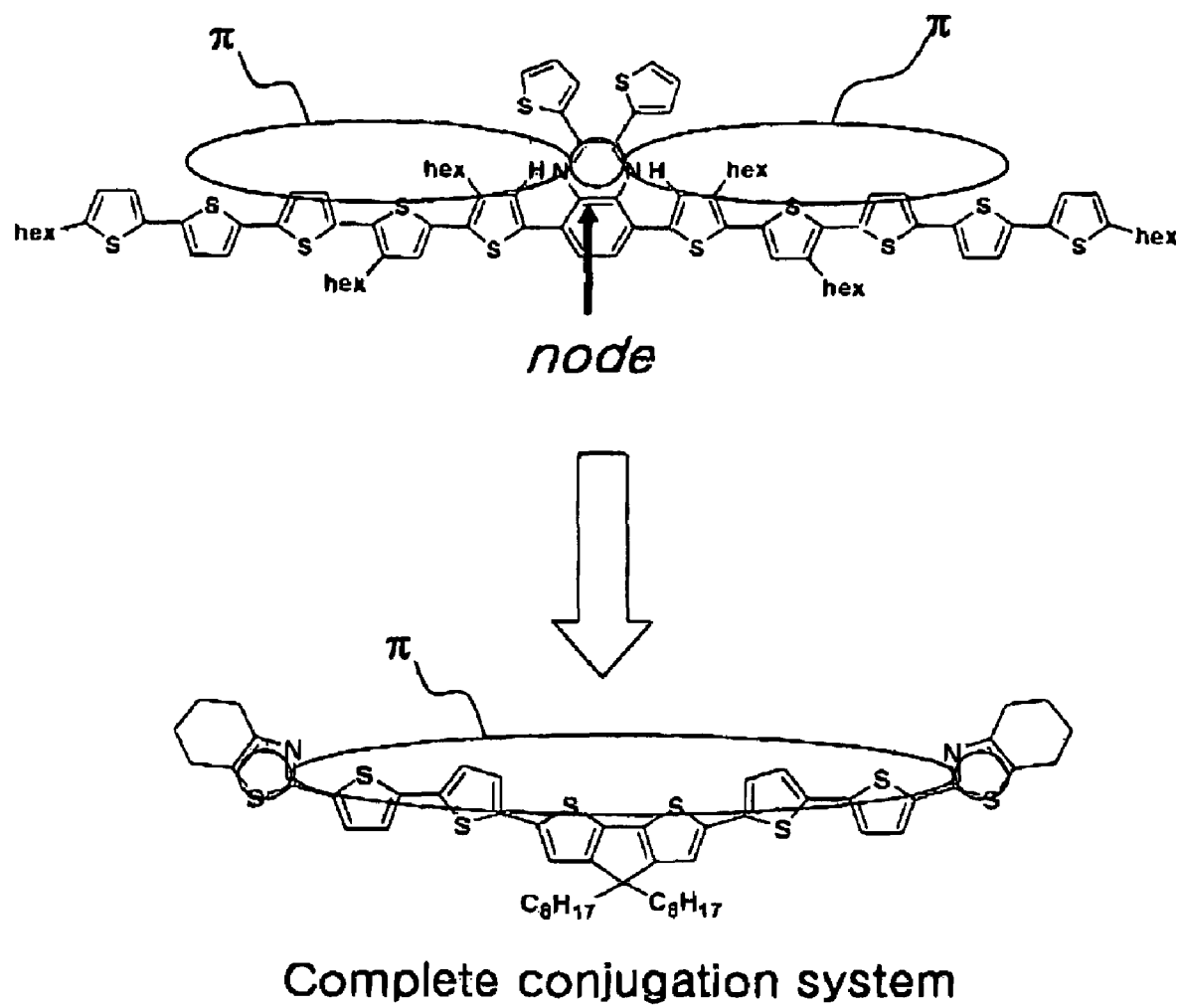
FIG. 1 illustrates the relative structure of both a PNP-type organic semiconductor compound having a distinct node structure and an NPN-type aromatic ring compound according to the invention illustrating the improved conjugation.

It should be noted that these Figures are intended to illustrate the general characteristics of organic semiconductor compounds and semiconductor device structures according to certain example embodiments to supplement the written description provided below. These drawings are not, however, to scale and may not precisely reflect the characteristics of any given embodiment, and should not be interpreted as defining or limiting the range of values or properties of embodiments within the scope of this invention. In particular, the relative positioning and sizing of atoms, bonds, layers or regions may be reduced or exaggerated for clarity.

DESCRIPTION OF EXAMPLE EMBODIMENTS

Hereinafter, a detailed description will be given of example embodiments, with reference to the appended drawings.

The NPN-type aromatic ring compounds of example embodiments may be represented by Formula I below:

(I)

wherein each X is independently selected from the group consisting of unsubstituted and substituted C6-C30 aryl groups and a substituted and unsubstituted C2-C20 heteroaryl groups containing sulfur (S) or selenium (Se), $A_1$ and $A_2$ are each independently selected from a C2-C20 heteroaryl group containing nitrogen (N) or oxygen (O), and further wherein n is an integer from 2 to 10.

Each of the n X groups incorporated in Formula I, which comprise the P-type portion of the NPN-type structure, may be selected from the groups represented by the structures illustrated below, which include at least one thiophene group and/or phenyl group for increasing the carrier mobility in the resulting semiconductor:

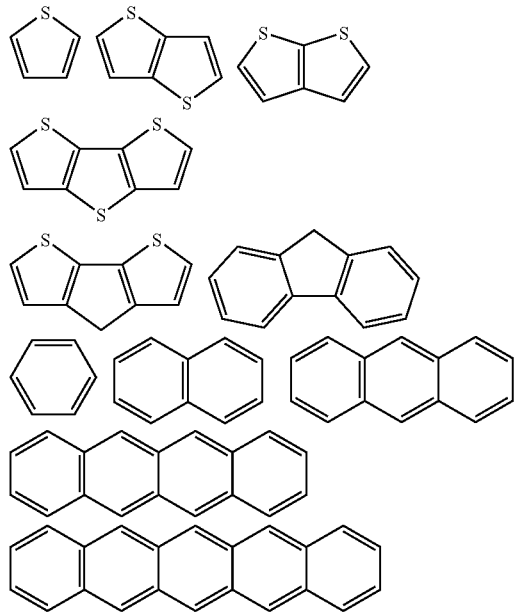

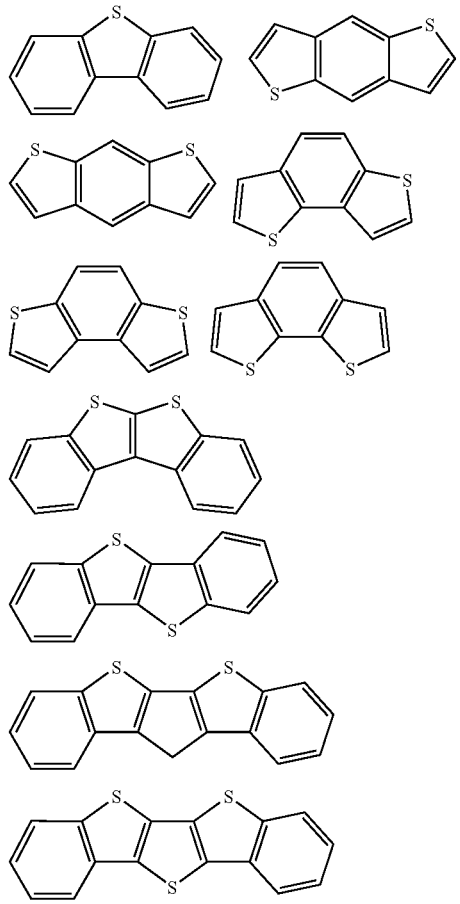

In Formula I, $A_1$ and $A_2$, each of which has an N-type aromatic structure tending to donate electrons, may be independently selected from the groups represented by the structures illustrated below, each of which include at least one heterogeneous aromatic ring that contains at least one nitrogen atom:

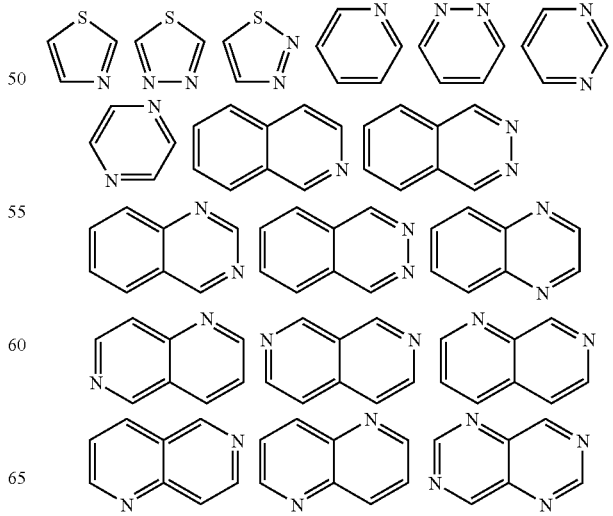

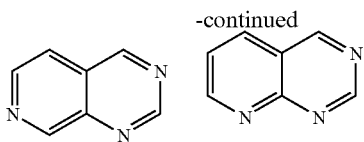

Typically, the plastic substrates used in the conventional fabrication of flexible display devices cannot endure a heat-curing temperature of about 150° C. or more. Accordingly, organic semiconductor materials that required higher temperature processing were generally incompatible with the lighter and more flexible plastic substrates, thereby incurring increased weight and reduced flexibility. However, the low molecular weight NPN-type aromatic ring compounds according to example embodiments include linear conjugated chains and may be processed under conditions compatible with plastic substrates. Accordingly, the NPN-type aromatic ring compounds according to example embodiments may be used to manufacture organic semiconductor thin films on such plastic substrates using solution-based processes at temperatures below 150° C., for example, at room temperature of about 25° C. In addition, the NPN-type aromatic ring compounds according to example embodiments exhibit a more complete π-conjugation system generally centered within the compound, thereby providing organic semiconductor thin films exhibiting improved electrical and chemical stability.

FIG. 1 illustrates both a conventional PNP-type organic semiconductor material and an NPN-type organic semiconductor material according to the invention. As shown in FIG. 1, the PNP-type semiconductor material has a structure in which the P-type π-conjugation region is distributed on opposite sides of the N-type core. Accordingly, even though the number of P-type aromatic regions is increased relative to an NPN-type structure, the current capacity tends to be decreased when the resulting transistor is the on-state and the leakage current tends to be increased when the resulting transistor is in the off-state. It is suspected that the increased leakage current may be a function of semiconductor material that when exposed to an oxidizing ambient, for example, air, tends to become readily oxidized to at least some degree.

The aromatic ring compounds according to the invention, however, are structured in a manner such that N-type aromatic structures configured for donating electrons are disposed on both sides of a P-type aromatic ring able to be π-conjugated, therefore realizing an aromatic system in which the center of the compound is completely conjugated. When one or more such aromatic ring compounds are applied to devices in practice, the oxidation potential will be more uniform and a more stable organic semiconductor thin film may be formed. Further, because the compounds according to example embodiments have relatively low molecular weights, they may be more easily and efficiently dissolved in an organic solvent or organic solvent system to render them suitable for application using conventional coating processes, for example, spin coating processes, at or near room temperature. Accordingly, the aromatic ring compounds according to the invention will have a weight average molecular weight (Mw) from 300 to 5,000.

In Formula I, $A_1$, $A_2$ and each of the n X groups may be unsubstituted or may be independently substituted by one or more substituents selected from a group consisting of halogen elements, a nitro group, an amino group, a cyano group, a hydroxyl group, unsubstituted and substituted C1-C20 alkyl groups, unsubstituted and substituted C2-C20 alkenyl groups, unsubstituted and substituted C2-C20 alkynyl groups, unsubstituted and substituted C1-C20 alkoxy groups, unsubstituted and unsubstituted C6-C20 arylalkyl groups, unsubstituted and substituted C6-C30 aryloxy groups, unsubstituted and substituted C2-C30 heteroaryloxy groups, unsubstituted and substituted C1-C20 heteroalkyl groups, unsubstituted and substituted C2-C30 heteroarylalkyl groups, and unsubstituted and substituted C3-C20 fused alkyl groups.

Examples embodiments of the aromatic ring compounds generally represented by Formula I may include, for example, the compounds represented by Formulas IV to VI below:

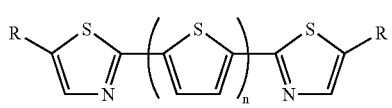

(IV)

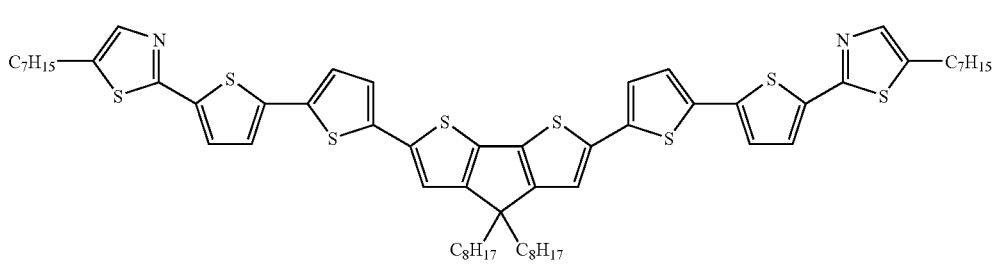

(V)

-continued

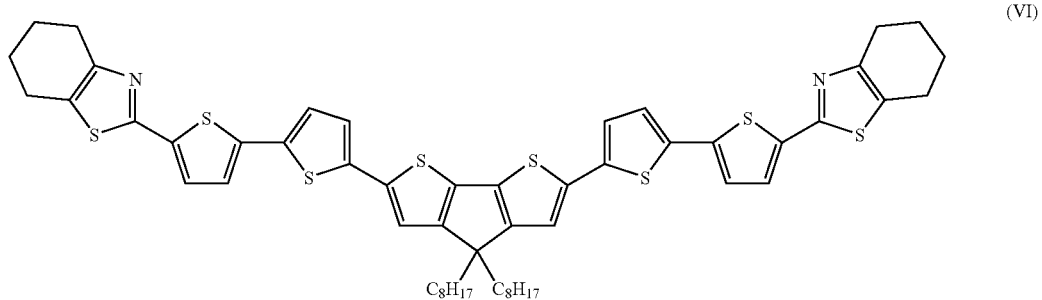

(VI)

in Formulas IV to VI, R and R' are each independently selected from the group consisting of halogen elements, a nitro group, an amino group, a cyano group, a hydroxyl group, unsubstituted and substituted C1-C20 alkyl groups, unsubstituted and substituted C2-C20 alkenyl groups, unsubstituted and substituted C2-C20 alkynyl groups, unsubstituted and substituted C1-C20 alkoxy groups, unsubstituted and substituted C6-C20 arylalkyl groups, unsubstituted and substituted C6-C30 aryloxy groups, unsubstituted and substituted C2-C30 heteroaryloxy groups, unsubstituted and substituted C1-C20 heteroalkyl groups, unsubstituted and substituted C2-C30 heteroarylalkyl groups, and unsubstituted and substituted C3-C20 fused alkyl groups.

Other examples embodiments of aromatic ring compounds include compounds represented by Formulas VIII-X below:

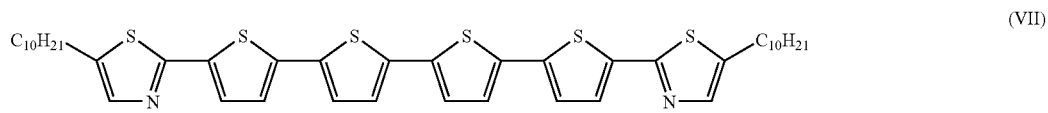

(VII)

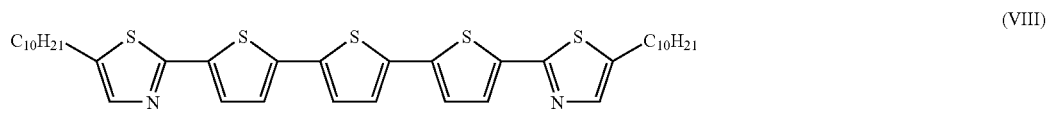

(VIII)

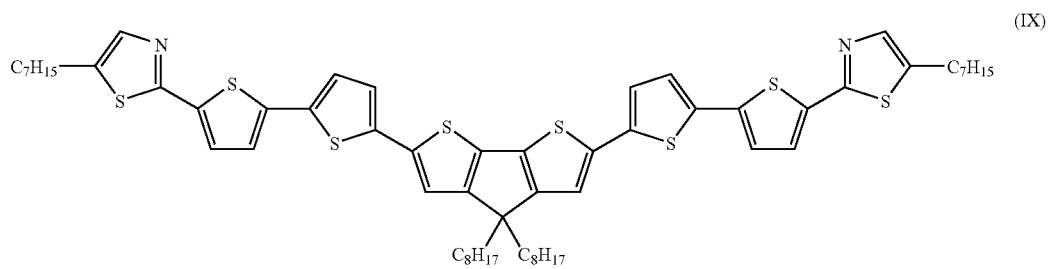

(IX)

-continued

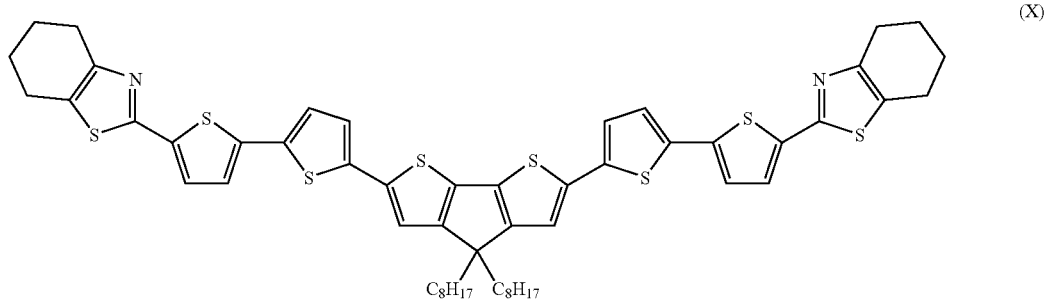

(X)

The aromatic ring compounds according to the invention may be formed using a general synthesis process, for example, chemical and/or electrochemical oxidation synthesis processes typically utilized for polymerization of heteroaromatic compounds, or a polycondensation process using an organic transition metal compound for example, nickel or palladium, but the compounds according to the invention are not limited to any particular synthesis technique but may be synthesized using any useful reagents, catalysts or methods.

The invention also includes organic semiconductor materials, which may be configured as layers and/or patterns, formed using one or more of the aromatic ring compounds according to example embodiments. The organic semiconductor materials according to the invention may be formed by applying a precursor solution including at least one aromatic ring compound according to Formula I and at least one organic solvent to a substrate to form a coating film. This coating film is then heat treated to evaporate the solvent(s) and thus obtain an organic semiconductor thin film. The total weight of the aromatic ring compound(s)
incorporated in the precursor solution may account for 0.01 to 30 wt % based on the total weight of the precursor solution.

The organic solvent(s) used in preparing the precursor solution may include at least one solvent selected from a group consisting of aliphatic hydrocarbon solvents, for example, hexane or heptane, aromatic hydrocarbon solvents, for example, toluene, pyridine, quinoline, anisol, mesitylene, or xylene, ketone-based solvents, for example, methyl isobutyl ketone, 1-methyl-2-pyrrolidinone, cyclohexanone, or acetone, ether-based solvents, for example, tetrahydrofuran, or isopropyl ether, acetate-based solvents, for example, ethyl acetate, butyl acetate, or propylene glycol methyl ether acetate, alcohol-based solvents, for example, isopropyl alcohol, or butyl alcohol, amide-based solvents, for example, dimethylacetamide, or dimethylformamide, silicon-based solvents, and mixtures thereof. The precursor solution may also include other components including, for example, viscosity modifiers and surfactants, to obtain a precursor solution having a desired combination of properties suitable for forming a coating film of sufficient thickness and uniformity.

The precursor solution including the aromatic ring compound(s) according to example embodiments and the organic solvent(s) may then be applied to a substrate, for example, by spin coating, to form a coating film having. The substrate is not particularly limited so long as it does is compatible with the precursor solution, the aromatic ring compound(s) according to example embodiments and any subsequent processing required to form an organic semiconductor layer from the precursor solution. Such substrates may include, for example, glass substrates, semiconductor wafers, ITO glass substrates, quartz substrates, silica-coated substrates, alumina-coated substrates, plastic substrates, that are suitable for both the intended end use of the semiconductor devices that will utilize the organic semiconductor layer and any subsequent processing necessary to create such devices.

The precursor solution may be applied to the substrates using a coating process, for example, spin coating, dip coating, roll-to-roll coating, screen coating, spray coating, spin casting, flow coating, screen printing, ink jetting, and drop casting. Of these coating processes, spin coating processes are generally expected to provide acceptable results, as a consequence of the knowledge obtained from the other spin coating processes present throughout semiconductor fabrication processes, can be both simple and inexpensive to implement and can easily be adjusted to provide acceptable layer thickness and uniformity. The actual sequences utilized in such spin coating processes may vary somewhat, but it is anticipated that spin coating processes utilizing a spin speed in the range from 100 to 10,000 rpm will be capable of producing acceptable coating films on most substrates.

Once the coating film has been formed on the substrate, the coating film is then subjected to a thermal treatment to convert the coating film into the desired organic semiconductor thin film. The thermal treatment may be conducted at a treatment temperature of, for example, 40 to 250° C., depending on the compound(s) and the substrate being utilized, and may be initiated under a vacuum or may be conducted under an atmosphere of nitrogen, argon, air or mixtures thereof. As will be appreciated by those skilled in the art, the pressure and gas content to which the coating film is exposed during the thermal treatment may also be varied throughout the course of the treatment to provide, for example, increased solvent removal during the early portions of the treatment and suppressed oxidation during the later portions of the treatment. The duration of the thermal treatment may range from 1 to 100 minutes and may be conducted under a generally uniform temperature or may be conducted under varying temperatures, for example, with the treatment temperature gradually increasing over the duration of the thermal treatment or with more complex temperature profiles including, for example, a temperature ramp up, followed by a hold period, followed by a temperature ramp down.

The organic semiconductor layers resulting from this thermal treatment of the coating film tend to exhibit improved chemical and electrical stability that may be attributable, at least in part, to its NPN-type structure which alleviates instability associated with the PNP-type structures and their relatively higher fraction of P-type compared to N-type structure. Further, when the organic semiconductor layer is being utilized as a carrier transport layer in an electronic device, the availability of room-temperature solution-based application processes can provide both capital and fabrication cost reductions. Specific examples of electronic devices that could incorporate an organic semiconductor layer according to example embodiments include, for example, organic thin film transistors, electroluminescent devices, solar cells, and memory devices.

A further understanding may be obtained by reviewing and considering the following example embodiments which are set forth to illustrate, but which are not to be construed to limit the scope of the claims.

PREPARATIVE EXAMPLE 1

Synthesis of Example Aromatic Ring Compound A

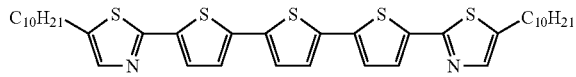

An example embodiment of a synthesis sequence for preparing Compound A is illustrated below:

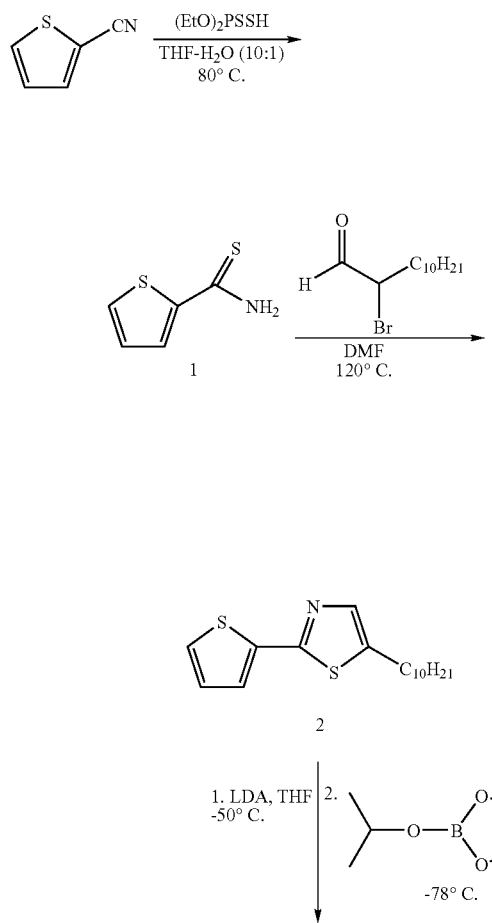

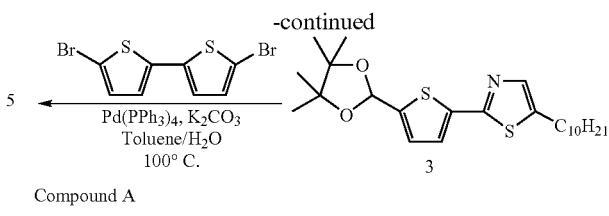

Compound A 5.5 g (55 mmol) of 2-cyanothiophene was combined with a mixture of 100 ml of tetrahydrofuran and 10 ml of water, thereby forming a mixture to which 20 ml (110 mmol) of dithiophosphonic acid 0,0-diethylether was slowly added to form a reaction mixture. This reaction mixture was then heated with reflux at 80° C. for 8 hours, poured into ethyl acetate, and then washed three times with water. The organic layer was then filtered using silica gel and a 1:2 hexane/ethyl acetate solvent system to obtain a yellow solution. This yellow solution was then distilled under vacuum to remove the solvent, thereby yielding about 10 g of a reaction product 1.

2.8 g (19 mmol) of the reaction product 1 was then mixed with 6.8 g (28.5 mmol) of 2-bromododecyl aldehyde in a DMF solvent and heated at 120° C. for 8 hours to form another reaction mixture. The reaction mixture was then poured into ethyl acetate and washed three times with water. The organic layer was then dried over $MgSO_4$ and filtered. The filtrate was then distilled under vacuum to remove the solvent and purified via silica gel column chromatography using toluene, thus obtaining 2.64 g of a reaction product 2. Analysis of the reaction product 2 produced the following NMR data $^1$H-NMR (300 MHz, $CDCl_3$) δ(ppm) 0.88 (t, 3H, J=6.8 Hz), 1.26-1.33 (m, 14H), 1.63-1.70 (m, 2H), 2.81 (t, 2H, J=7.5 Hz), 7.05 (dd, 1H, J=5.0 and 4.4 Hz), 7.34 (dd, 1H, J=5.1 and 7.1 Hz), 7.35-7.43 (m, 2H).

2.64 g (8.58 mmol) of the reaction product 2 was then added to 5.15 ml (12.88 mmol) of lithium diisopropylamide (LDA) in a tetrahydrofuran solvent at −78° C. to which 2.1 ml (10.3 mmol) of dioxaborolane was then added to form a reaction mixture. The temperature of the reaction mixture was allowed to increase gradually to room temperature and reacted for an additional 8 hours. The resulting reaction solution was washed with an aqueous solution of ammonium chloride, after which the organic layer was dried over MgSO4 and then filtered. The filtrate was distilled under vacuum to remove the solvent, thus obtaining 3.7 g of a reaction product 3 without further purification. Analysis of the reaction product 3 produced the following NMR results: $^1$H-NMR (300 MHz, $CDCl_3$) δ(ppm) 0.88 (t, 3H, J=6.8 Hz), 1.14-1.43 (m, 26H), 1.63-1.72 (m, 2H), 2.82 (t, 2H, J=7.5 Hz), 7.44 (s, 1H), 7.50 (d, 1H, J=3.7 Hz), 7.55 (d, 1H, J=3.7 Hz).

1.67 g (3.85 mmol) of thiophene borolane 3 (reaction product 3) was then added along with 0.5 g (1.54 mmol) of 2,2'-dibromobithiophene to a mixture of toluene and water. 115 mg (0.1 mmol) of Pd(PPh$_3$)$_4$ [tetrakis(triphenylphosphine) palladium (0) (Aldrich)] and 138 mg (1 mmol) of potassium carbonate were then added and then the reaction mixture was reacted at 110° C. for 8 hours. The resulting reaction solution was then washed with an aqueous solution of ammonium chloride, after which the organic layer was dried over MgSO$_4$ and then filtered. The filtrate was distilled under vacuum to remove the solvent and then purified via silica gel column chromatography using chloroform, thus yielding the compound A. Analysis of compound A produced the following NMR data: $^1$H-NMR (300 MHz, CDCl$_3$) δ(ppm) 0.88 (t, 6H, J=6.8 Hz), 1.20-1.43 (m, 28H), 1.64-1.69 (m, 4H), 2.83 (t, 4H, J=7.5 Hz), 7.12-7.16 (m, 6H), 7.29-7.33 (m, 2H), 7.43 (s, 2H).

PREPARATIVE EXAMPLE 2

Synthesis of Example Aromatic Ring Compound B

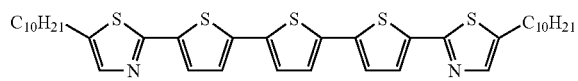

An example embodiment of a synthesis sequence for preparing Compound B is illustrated below:

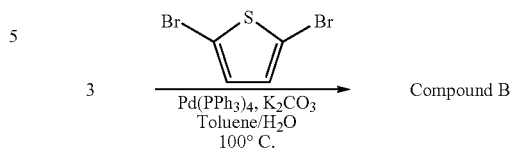

2 g (2.88 mmol) of thiophene borolane 3 (reaction product 3) was added along with 0.4 g (1.65 mmol) of 2,5-dibromobithiophene to toluene and water. 115 mg (0.1 mmol) of Pd(PPh$_3$)$_4$ and 138 mg (1 mmol) of potassium carbonate were then added to complete the reaction mixture thereto, and then the reaction mixture was reacted at 110° C. for 8 hours. The resulting reaction solution was washed with an aqueous solution of ammonium chloride and water, and the organic layer was dried over MgSO$_4$ and then filtered. The filtrate was distilled under vacuum to remove the solvent and then purified via silica gel column chromatography using chloroform, thus obtaining the compound B. Analysis of compound B produced the following NMR data: $^1$H-NMR (300 MHz, CDCl$_3$) δ(ppm) 0.88 (t, 6H, J=6.8 Hz), 1.20-1.43 (m, 28H), 1.64-1.69 (m, 4H), 2.83 (t, 4H, J=7.5 Hz), 7.12 (d, 2H, J=3.8 Hz), 7.15 (s, 2H), 7.32 (d, 2H, J=3.8 Hz), 7.72 (s, 2H).

PREPARATIVE EXAMPLE 3

Synthesis of Example Aromatic Ring Compound C

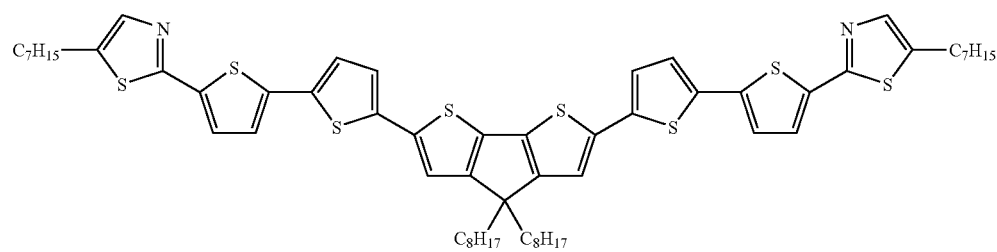

An example embodiment of a synthesis sequence for preparing Compound C is illustrated below:

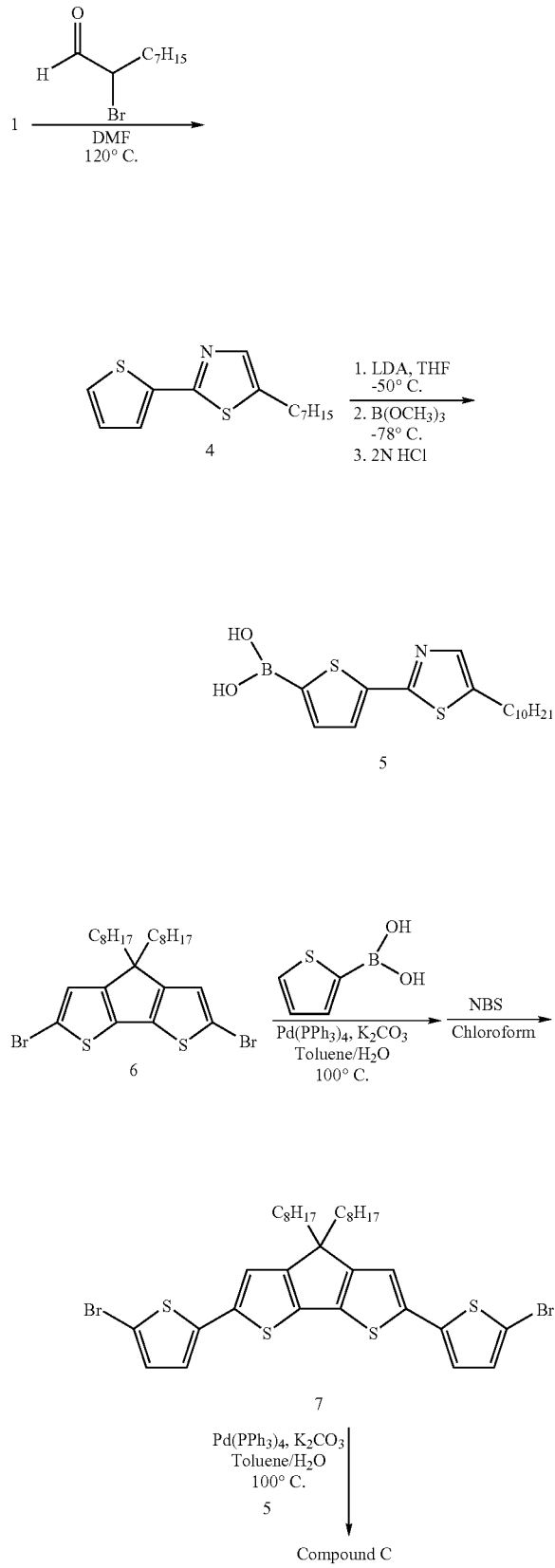

2.8 g (19 mmol) of the reaction product 1 was mixed with 3 g (13.6 mmol) of 2-bromononyl aldehyde in a DMF solvent, after which the reaction mixture was heated at 120° C. for 8 hours. The heated reaction mixture was then poured into ethyl acetate and washed three times with water, after which the organic layer was dried over $MgSO_4$ and then filtered. The filtrate was distilled under vacuum to remove the solvent and then purified via silica gel column chromatography using toluene, thus obtaining 2 g of a reaction product 4. Analysis of the reaction product 4 produced the following NMR data: $^1$H-NMR (300 MHz, $CDCl_3$) δ(ppm) 0.89(t, 3H, J=6.9 Hz), 0.86-0.39 (m, 8H), 1.65-1.70 (m, 2H), 2.82 (t, 3H, J=7.8 Hz), 7.06 (t, 1H, J=5.1 Hz), 7.35 (d, 1H, J=5.1 Hz), 7.41-7.43 (m, 2H).

2 g (7.11 mmol) of the reaction product 4 was then reacted with 10 ml (10 mmol) of LDA (1 N) in a tetrahydrofuran solvent at −78° C. and then combined with 1 ml (8.53 mmol) of trimethylborate, after which the temperature of the reaction mixture was gradually increased to room temperature. After the reaction mixture reacted for 8 hours at room temperature with agitation, it was poured into an aqueous solution of 2N HCl and agitated for an additional 1 hour. This reaction mixture was then reacted for an additional 8 hours, after which the resulting reaction solution was washed with an aqueous solution of ammonium chloride, the organic layer was dried over $MgSO_4$ and then filtered. The filtrate was distilled under vacuum to remove the solvent, thus obtaining 1.5 g of a reaction product 5 without further purification. Analysis of the reaction product produced the following NMR data: $^1$H-NMR (300 MHz, DMSO-d6) δ(ppm) 0.90(t, 6H, J=6.9 Hz), 1.29-1.39 (m, 16H), 1.63-1.67 (m, 4H), 2.86 (t, 6H, J=7.4 Hz), 7.57 (s, 2H), 7.59 (d, 2H, J=3.6 Hz), 7.66 (d, 2H, J=3.6 Hz), 8.43 (s, 4H).

1 g (1.79 mmol) of dibromide 6 and 0.69 g (5.37 mmol) of thiophene boronic acid were added to toluene and water. 200 mg (0.18 mmol) of $Pd(PPh_3)_4$ and 138 mg (1 mmol) of potassium carbonate were then added, after which the reaction mixture was reacted at 110° C. for 8 hours. The resulting reaction solution was washed with an aqueous solution of ammonium chloride, after which the organic layer was dried over $MgSO_4$ and then filtered. The filtrate was distilled under vacuum to remove the solvent, and then purified via silica gel column chromatography using hexane to prepare a polycondensed compound. This polycondensed compound was then reacted with 0.47 g (2.63 mmol) of N-bromosuccinimide in a chloroform solvent, thus obtaining 0.88 g of a reaction product 7. Analysis of the reaction product 7 produced the following NMR data:
$^1$H-NMR (300 MHz, $CDCl_3$) δ(ppm) 0.84 (t, 3H, J=6.9 Hz), 0.91-0.99 (m, 2H), 1.15-1.27 (m, 10H), 1.79-1.85 (m, 2H), 6.90 (d, 1H, J=3.8 Hz), 6.94 (s, 1H), 6.96 (d, 1H, J=3.8 Hz).

0.44 g (0.61 mmol) of dibromide reaction product 7 and 0.59 g (1.83 mmol) of boronic acid 5 were added to toluene and water, and 100 mg (0.09 mmol) of $Pd(PPh_3)_4$ and 138 mg (1 mmol) of potassium carbonate were added thereto, and then the reaction mixture was reacted at 110° C. for 8 hours. The resulting reaction solution was washed with an aqueous solution of ammonium chloride, after which the organic layer was dried over $MgSO_4$ and then filtered. The filtrate was distilled under vacuum to remove the solvent, and then purified via silica gel column chromatography using hexane, thus obtaining the compound C. Analysis of compound C produced the following NMR data: $^1$H-NMR (300 MHz, $CDCl_3$) δ(ppm) 0.81-0.93 (m, 12H), 0.93-1.17 (m, 4H), 1.17-1.37 (m, 36H), 1.66-1.71 (m, 4H), 1.86-1.88 (m, 4H), 2.82 (t, 4H, J=7.4 Hz), 7.03 (s, 2H), 7.06-7.10 (m, 4H), 7.13 (d, 2H, J=3.8 Hz), 7.32 (d, 2H, J=3.8 Hz), 7.42 (d, 2H).

PREPARATIVE EXAMPLE 4

Synthesis of Example Aromatic Ring Compound D

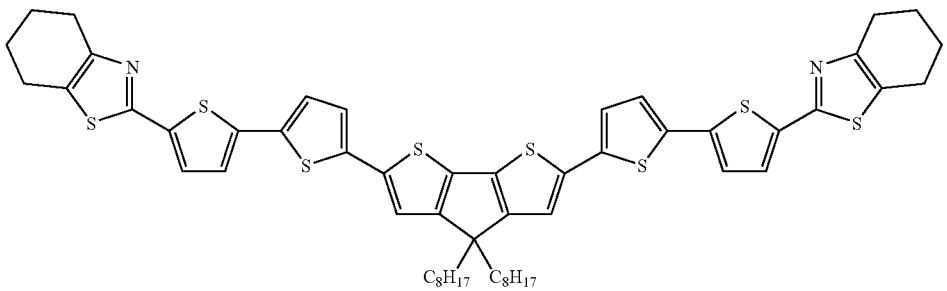

An example embodiment of a synthesis sequence for preparing Compound D is illustrated below:

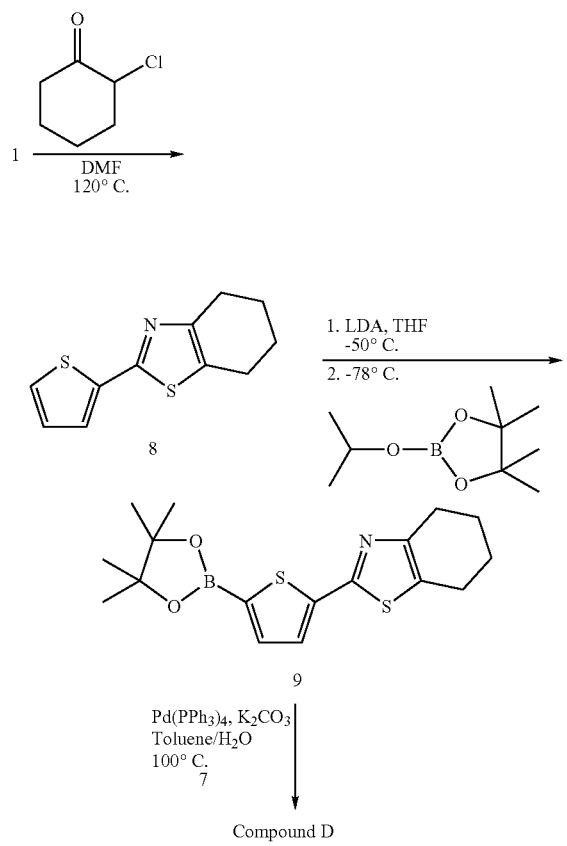

5 g (34.9 mmol) of the reaction product 1 was mixed with 5.5 g (41.9 mmol) of 2-chlorocyclohexanone in a DMF solvent, and then the mixture was heated at 120° C. for 8 hours. The heated mixture was poured into ethyl acetate and then washed three times with water, after which the organic layer was dried over $MgSO_4$ and then filtered. The filtrate was distilled under vacuum to remove the solvent and then purified via silica gel column chromatography using toluene, thus obtaining a reaction product 8. Analysis of the reaction product 8 produced the NMR data
$^1$H-NMR (300 MHz, $CDCl_3$) δ(ppm) 1.71-1.91 (m, 4H), 2.77-2.82 (m, 4H), 7.04 (dd, 1H, J=5.0 and 3.7 Hz), 7.31 (dd, 1H, J=5.0 and 3.8 Hz), 7.41 (d, 1H, J=3.7 Hz).

4.7 g (21.2 mmol) of the reaction product 8 was then added with 31.8 ml (31.8 mmol) of LDA (1 N) in a tetrahydrofuran solvent at −78° C. and then with 5.2 ml (25.4 mmol) of dioxaborolane. The temperature of the reaction mixture was gradually increased to room temperature and reacted for 8 hours at room temperature. The resulting reaction solution was then washed with an aqueous solution of ammonium chloride, and then the organic layer was dried over $MgSO_4$ and then filtered. The filtrate was distilled under vacuum to remove the solvent, thus obtaining 5 g of a reaction product 9 without further purification. Analysis of the reaction product 9 produced the following NMR data: $^1$H-NMR (300 MHz, $CDCl_3$) δ(ppm) 1.34 (s, 12H), 1.87-1.90 (m, 4H), 2.79-2.82 (m, 4H), 7.50 (d, 1H, J=3.6 Hz), 7.54 (d, 1H, J=3.6 Hz)

0.66 g (1.90 mmol) of thiophene borolane (reaction product 9) was added, along with 0.46 g (0.63 mmol) of dibromide 7 (reaction product 7) to toluene and water. 0.3 g (0.26 mmol) of $Pd(PPh_3)_4$ and 138 mg (1 mmol) of potassium carbonate were then added, after which the reaction mixture was reacted at 110° C. for 8 hours. The resulting reaction solution was washed with an aqueous solution of ammonium chloride, after which the organic layer was dried over $MgSO_4$ and then filtered. The filtrate was distilled under vacuum to remove the solvent, and then purified via silica gel column chromatography using chloroform, thus obtaining the compound D. Analysis of compound D produced the following NMR data: $^1$H-NMR (300 MHz, $CDCl_3$) δ(ppm) 0.84 (t, 6H, J=6.9 Hz), 0.9-1.0 (m, 4H), 1.17-1.25 (m, 20H), 1.83-1.89 (m, 12H), 2.79-2.82 (m, 8H), 7.03 (s, 2H), 7.09 (t, 4H, J=4.1 Hz), 7.13 (d, 2H, J=3.8 Hz), 7.32 (d, 2H, J=3.9 Hz).

APPLICATION EXAMPLE 1

Example Fabrication of Organic Thin Film Transistor

On a washed plastic substrate, aluminum/niobium (Al/Nb) alloy, serving as a gate electrode, was deposited to a thickness of 1000 Å using a sputtering process, and then $SiO_2$, serving as a gate insulating film, was deposited to a thickness of 1.4 μm via chemical vapor deposition (CVD).

Subsequently, a conductive layer, for example gold (Au), was deposited to a thickness of 1200 Å using a sputtering process, patterned and etched to form the source/drain electrodes. Before the organic semiconductor material substrate was deposited on the substrate, the substrate was washed using isopropyl alcohol for 10 min and then dried. In preparation for the layer formation, the substrate was then immersed in a 10 mM solution of octadecyltrichlorosilane in hexane for 30 seconds, washed with acetone, and then dried. The example aromatic ring compound A obtained as described above in Preparative Example 1 was dissolved at a concentration of 0.1 wt % in a xylene solvent and applied to the substrate to form a coating film.

Figure 2:
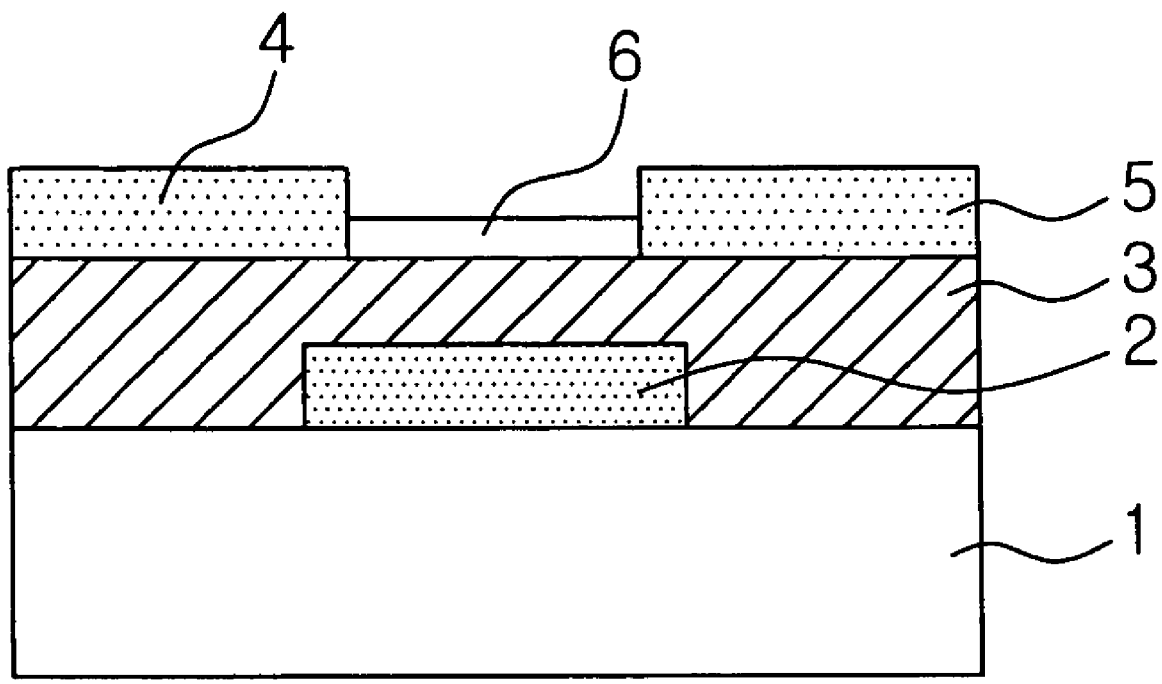
FIG. 2 is a cross-sectional view illustrating an organic thin film transistor incorporating a region of an NPN-type aromatic ring compound according to the invention.

The coating film was then baked at 150° C. for 30 minutes under in an argon atmosphere to form an organic semiconductor layer incorporated in the bottom-contact-type organic thin film transistor shown in FIG. 2. As shown in FIG. 2, the semiconductor device includes the substrate 1, the gate pattern 2, the gate dielectric 3, the source/drain region patterns 4,5 and the organic semiconductor region 6 provided between the source/drain regions.

APPLICATION EXAMPLES 2-4

Example Fabrication of Organic Thin Film Transistors

Respective organic thin film transistors were manufactured in the same manner as described above in Application Example 1, with the exception that each of the example aromatic ring compounds B, C and D which were synthesized as detailed in Preparative Examples 2-4 was used as the material for forming an organic active layer.

In order to evaluate the electrical properties of the resulting organic thin film transistors fabricated from solutions of the example aromatic ring compounds synthesized in the manner detailed above in the Preparative Examples 1-4. The current transfer properties of the resulting organic thin film transistors were then measured using a semiconductor characterization system (4200-SCS), available from KEITHLEY Co. Ltd. These current transfer properties and other physical and parametric measurements were then used for calculating charge mobility and cut-off leakage current values for the resulting devices. The results of this evaluation are provided in Table 1 below.

The charge mobility was calculated using the above current transfer curve and the following current equation for the saturation region. That is, the current equation for the saturation region was converted into a graph relating $(I_{SD})^{1/2}$ to $V_G$, and the charge mobility was calculated from the slope of the converted graph:

$$I_{SD} = \frac{WC_0}{2L}\mu(V_G - V_T)^2$$

$$\sqrt{I_{SD}} = \sqrt{\frac{\mu C_0 W}{2L}}(V_G - V_T)$$

$$\text{slope} = \sqrt{\frac{\mu C_0 W}{2L}}$$

$$\mu_{FET} = (\text{slope})^2 \frac{2L}{C_0 W}$$

wherein $I_{SD}$ is source-drain current; $\mu$ or $\mu_{FET}$ is charge mobility; $C_O$ is oxide film capacitance; W is channel-width; L is channel length; $V_G$ is gate voltage; and $V_T$ is threshold voltage.

The cut-off leakage current ($I_{off}$), which is the current flowing in the off-state, was determined to be the minimum current in the off-state.

TABLE 1

| Organic Active Layer | Charge Mobility (cm²/V-s) | Cut-off Leakage Current (A) |
|---|---|---|
| App. Ex. 1 | $10^{-4}$ | $10^{-11}$ |
| App. Ex. 2 | $5 \times 10^{-5}$ | $10^{-12}$ |
| App. Ex. 3 | $5 \times 10^{-4}$ | $10^{-11}$ |
| App. Ex. 4 | $10^{-4}$ | $10^{-11}$ |

As is apparent from TABLE 1, the transistors manufactured using the aromatic ring compounds according to the invention were confirmed to have relatively low cut-off leakage currents of $10^{-11}$ A or less while generally maintaining the overall performance of the resulting devices. Therefore, when one or more of the aromatic ring compounds according to example embodiments are applied to various electronic devices, for example, thin film transistors, electroluminescent devices, solar cells, and memory, an organic semiconductor thin film having excellent electrical properties can be fabricated.

As described hereinbefore, the invention provides for the production of a range of NPN-type low molecular aromatic ring compounds, as well as organic semiconductor layers and electronic device incorporating such layers. Because the aromatic ring compounds according to the invention may be applied using a solution-based "wet" process at or near room temperature of about 25° C. The application of these NPN-type low molecular organic semiconductor materials as detailed above to substrates in this manner is suitable for semiconductor fabrication processes requiring coverage of relatively large areas with a chemically and electrically stable organic semiconductor thin film. It is anticipated that the NPN-type organic semiconductors according to the invention can be successfully applied in the fabrication of a variety of electronic devices including, for example, organic thin film transistors, electroluminescent devices, solar cells, and memory devices.

Although example embodiments have been disclosed for illustrative purposes, those skilled in the art will appreciate that various modifications, additions and substitutions are possible, without departing from the scope and spirit of the following claims.

What is claimed is:

1. An NPN-type aromatic ring compound, which is represented by Formula I:

by Formula IV:

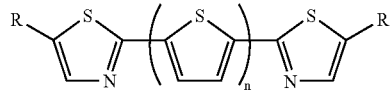

wherein each R group is the same or different, and preferably is selected from the group consisting of halogen elements, a nitro group, an amino group, a cyano group, a hydroxyl group, unsubstituted and substituted C1-C20 alkyl groups, unsubstituted and substituted C2-C20 alkenyl groups, unsubstituted and substituted C2-C20 alkynyl groups, unsubstituted and substituted C1-C20 alkoxy groups, unsubstituted and substituted C6-C20 arylalkyl groups, unsubstituted and substituted C6-C30 aryloxy groups, unsubstituted and substituted C2-C30 heteroaryloxy groups, unsubstituted and substituted C1-C20 heteroalkyl groups, unsubstituted and substituted C2-C30 heteroarylalkyl groups, and unsubstituted and substituted C3-C20 fused alkyl groups and further wherein n is an integer from 3 to 10.

2. The aromatic ring compound according to claim 1, wherein:

the compound is further represented by Formula VII:

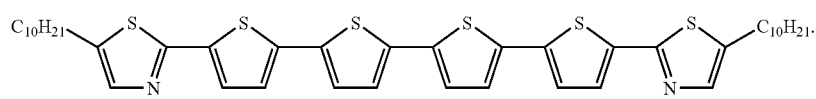

3. The aromatic ring compound according to claim 1, wherein:
the compound is further represented by Formula VIII:

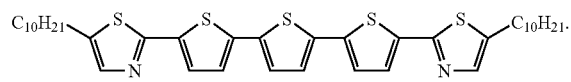

4. An NPN-type aromatic ring compound, which is represented by Formula I:
by Formula V:

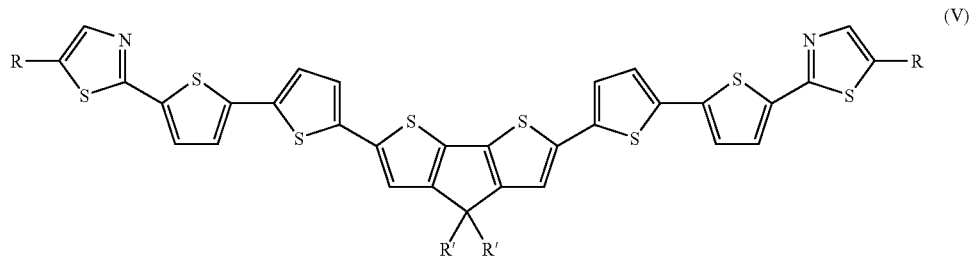

wherein each R and R' is the same or different and is independently selected from the group consisting of halogen elements, a nitro group, an amino group, a cyano group, a hydroxyl group, unsubstituted and substituted C1-C20 alkyl groups, unsubstituted and substituted C2-C20 alkenyl groups, unsubstituted and unsubstituted C2-C20 alkynyl groups, unsubstituted and substituted C1-C20 alkoxy groups, unsubstituted and substituted C6-C20 arylalkyl groups, unsubstituted and substituted C6-C30 aryloxy groups, unsubstituted and substituted C2-C30 heteroaryloxy groups, unsubstituted and substituted C1-C20 heteroalkyl groups, unsubstituted and substituted C2-C30 heteroarylalkyl groups, and unsubstituted and unsubstituted C3-C20 fused alkyl groups.

5. The aromatic ring compound according to claim 4, wherein:

the compound is further represented by Formula IX:

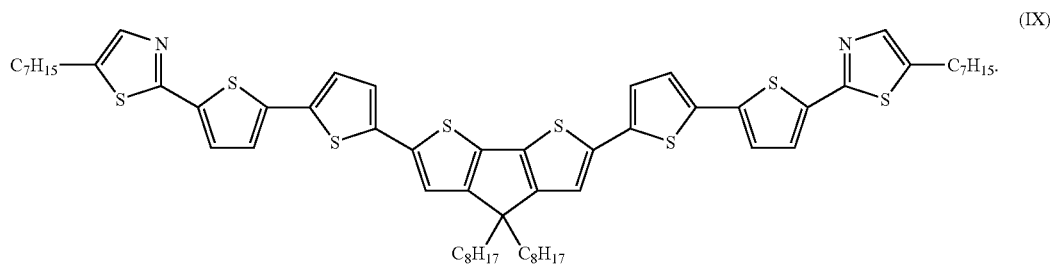

(IX)

6. An NPN-type aromatic ring compound, which is represented by Formula I:

by Formula VI below:

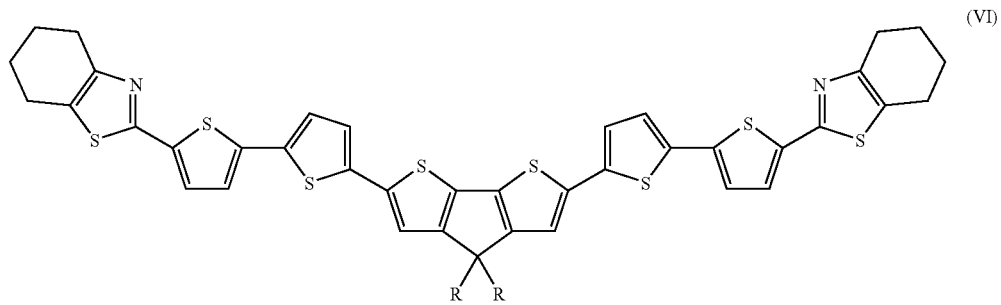

(VI)

wherein R is selected from the group consisting of halogen elements, a nitro group, an amino group, a cyano group, a hydroxyl group, unsubstituted and substituted C1-C20 alkyl group, unsubstituted and substituted C2-C20 alkenyl groups, unsubstituted and substituted C2-C20 alkynyl groups, unsubstituted and substituted C1-C20 alkoxy groups, unsubstituted and substituted C6-C20 arylalkyl groups, unsubstituted and substituted C6-C30 aryloxy groups, unsubstituted and substituted C2-C30 heteroaryloxy groups, unsubstituted and substituted C1-C20 heteroalkyl groups, unsubstituted and substituted C2-C30 heteroarylalkyl groups, and unsubstituted and substituted C3-C20 fused alkyl groups.

7. The aromatic ring compound according to claim 6, wherein:
the compound is further represented by Formula X:

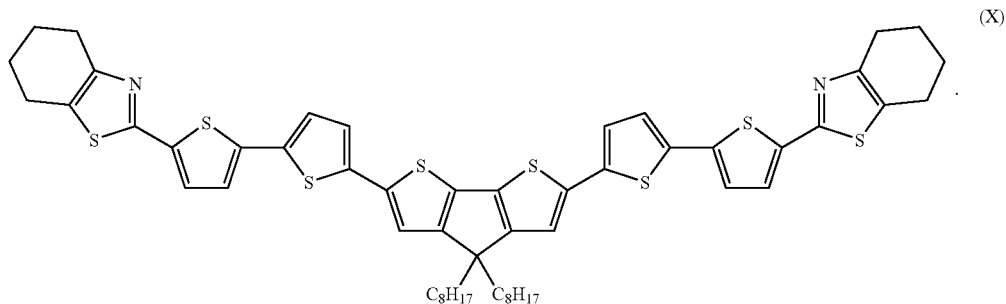

(X)